United States Patent [19]

Culp et al.

[11] Patent Number: 5,543,695
[45] Date of Patent: Aug. 6, 1996

[54] MEDICAL INSTRUMENT WITH PROGRAMMABLE TORQUE CONTROL

[75] Inventors: Jerry A. Culp, Oshtemo Township; Kevin J. Schemansky, Portage, both of Mich.

[73] Assignee: Stryker Corporation, Kalamazoo, Mich.

[21] Appl. No.: 369,170

[22] Filed: Jan. 5, 1995

Related U.S. Application Data

[63] Continuation of Ser. No. 167,737, Dec. 15, 1993, abandoned.

[51] Int. Cl.$^6$ ..................................... H02P 7/00
[52] U.S. Cl. ................... 318/432; 318/799; 318/806
[58] Field of Search .................... 318/432, 434, 318/798–812

[56] References Cited

U.S. PATENT DOCUMENTS

| Re. 30,356 | 8/1980 | Berman et al. | 433/131 |
|---|---|---|---|
| 4,486,176 | 12/1984 | Tardieu et al. | 433/133 |
| 4,568,283 | 2/1986 | Hotta et al. | 433/104 |
| 4,760,317 | 7/1988 | Hetzel et al. | 318/254 |
| 4,870,334 | 9/1989 | Iwasha et al. | 318/432 |
| 5,469,215 | 11/1995 | Nashiki | 318/432 |

OTHER PUBLICATIONS

Yuji Akiyama, Tadashi Hitomi Akira Tsukihashi & Sosuke Sunago, "Sensorless Brushless DC Motor Shrinks Stereo Player Size", Power/Conversion & Intelligent Motion, Jan., 1991, cover and pp. 28–32.

Primary Examiner—David S. Martin
Attorney, Agent, or Firm—Flynn, Thiel, Boutell & Tanis, P.C.

[57] ABSTRACT

A powered medical instrument includes a manually operable foot switch coupled to a motor control unit which in turn is coupled to an autoclavable handpiece containing a brushless sensorless electric motor driving a tool. The motor control arrangement includes a control panel through which a user can select a maximum torque value for the motor, and includes a torque limit circuit which limits the motor torque to the torque limit value selected by the user. The control panel also provides a digital display of actual motor speed and allows the user to digitally specify a maximum motor speed. The output of the foot switch is adjusted by a transfer function and then used to control motor speed, and the transfer function is adjusted as necessary to precisely conform the actual motor speed and thus the displayed speed to the selected maximum speed. The feedback path for the actual motor speed is entirely digital, so that a highly accurate value of actual speed is available for display and for adjustment of the transfer function.

30 Claims, 6 Drawing Sheets

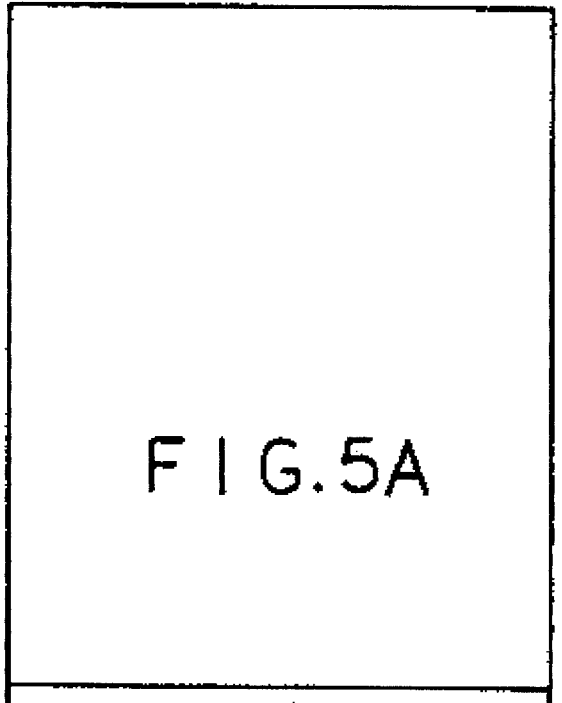
FIG. 5A
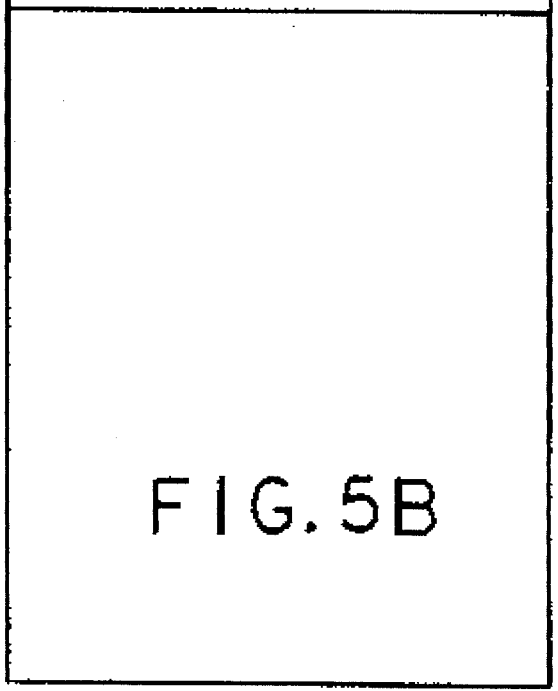
FIG. 5B
FIG. 5

MEDICAL INSTRUMENT WITH PROGRAMMABLE TORQUE CONTROL

This is a continuation of Ser. No. 08/167,737, filed Dec. 15, 1993, abandoned.

FIELD OF THE INVENTION

The present invention relates to a powered medical instrument and, more specifically, to a powered medical instrument having an electric motor which must be subjected to an autoclave, which must run precisely at a maximum speed specified digitally by a user, and which must be capable of having its torque limited to a user-selected value.

BACKGROUND OF THE INVENTION

One known type of powered medical instrument is a dental drill, including a handpiece containing an electric motor, a separate motor control unit detachably coupled to the handpiece, and a progressively actuatable foot switch used by an operator to vary the motor speed.

Conventional instruments of this type use brushless motors contain Hall sensors which are used to monitor motor operation. However, the handpiece containing the motor must be periodically subjected to high temperatures for purposes of sterilization, for example by being placed in an autoclave. This presents a problem, in that the high temperatures of an autoclave tend to destroy the Hall sensors in the motor. One known approach for protecting the Hall sensors is to hermetically seal them, but the sealed sensors are relatively large and prevent the motor from being relatively compact and lightweight, which is desirable in a handpiece.

Brushless motors which do not have sensors have been developed for other applications, such as rotationally driving the hard disk drive of a personal computer. However, these other applications typically involve a relatively simple motor control situation, because the motor is always operated at a predetermined fixed speed. In contrast, a powered medical instrument such as a dental drill must be capable of operation through a range of motor speeds and loads.

A further consideration is that, as digital technology has improved, the doctor or dentist using a dental drill is typically permitted to manually select a maximum motor speed for a given drilling operation, and during the drilling operation is able to watch the actual motor speed on a digital display. However, manufacturing tolerances of the motor and various components in the motor control arrangement can cause the actual speed to vary somewhat from the specified speed. For example, the motor speed constant, which is a function of manufacturing tolerances, may vary by 10% from motor to motor. While the actual speed may be reasonably close to the specified speed, the precise accuracy inherent in a digital display tends to make even small deviances appear significant, suggesting to the operator that the system is not fulfilling its responsibility of operating the motor exactly at the specified speed. Although it is theoretically possible to minimize such deviances by holding all critical components to very tight manufacturing tolerances, this significantly increases the cost of these components, and thus the cost of the overall system.

Still another consideration is that the electric motor used in a dental drill or similar medical instrument is often capable of producing torques which would break certain components within the drive train of the handpiece, and it is thus important to be able to limit motor torque to a value which avoids breakage. According to the present state of the art, the electric motor is usually operated by a motor control invertor having several pairs of transistors arranged in a totem pole configuration and controlled by complementary pulse width modulated control signals. Torque limiting schemes have previously been developed, but often limit the torque to a predetermined value which cannot be varied, and often have the effect of causing the transistors of the invertor to run in a linear mode rather than a switching mode, causing the transistors to generate more heat and thus necessitating the use of heat sinks and/or larger packages.

In view of the foregoing, one object of the present invention is to provide a powered medical instrument which utilizes a brushless sensorless motor and provides variable speed operation of the motor.

A further object is to provide a powered medical instrument having an arrangement for conforming actual motor speed to a digitally specified speed without requiring the use of strict manufacturing tolerances for the motor and certain components of the motor control arrangement.

A further object is to provide a powered medical instrument having a torque limiting arrangement which permits torque to be limited to a range of values while ensuring that the drive elements of an invertor controlling the motor always run in a switching mode and never in a linear mode, thereby substantially eliminating heat dissipation and avoiding heat sinks, while allowing tighter packaging.

SUMMARY OF THE INVENTION

The objects and purposes of the invention, including those set forth above, are met according to one form of the present invention by providing a powered medical instrument which includes a sensorless brushless electric motor, and a motor control arrangement coupled to the motor for operationally controlling the motor.

Another form of the present invention involves a powered medical instrument which includes: an electric motor; an arrangement for indicating a specified motor speed; a manually operable input device generating an output which varies from a first value to a second value as a function of varying manual operation; a motor control arrangement for causing the motor to run at a rotational speed which is a function of the output of the input device as adjusted by a function; an actual speed indicating arrangement for indicating a precise actual speed of the motor; and an adjusting arrangement responsive to the specified motor speed and the precise actual speed for adjusting the function when necessary to cause the motor to run substantially exactly at the specified motor speed when the output of the input device has the second value.

Still another form of the present invention involves an apparatus which includes: an electric motor; an arrangement for indicating a limit value representing a maximum motor torque; and a motor control arrangement for operationally controlling the motor, the motor control arrangement including an arrangement for producing a speed error output representing a difference between a setpoint and an actual speed of the motor, a torque limiting arrangement for producing an adjusted error output which is the lesser of the limit value and the magnitude of the speed error output, and an arrangement for supplying to the motor a quantity of motor current which corresponds to the magnitude of the adjusted error output.

One further form of the present invention involves an apparatus which includes: an electric motor; a limit specifying arrangement for indicating a limit value representing a maximum motor torque, the limit specifying arrangement including an arrangement for facilitating a selective change of the limit value; and a motor control arrangement for operationally controlling the motor, the motor control arrangement including an arrangement responsive to a difference between a setpoint and an actual speed of the motor for controlling motor current to reduce the difference, the motor control arrangement including an arrangement responsive to the limit value for limiting motor current to a value corresponding to the maximum motor torque represented by the limit value.

BRIEF DESCRIPTION OF THE DRAWINGS

A preferred embodiment of the invention is described in detail hereinafter with reference to the accompanying drawings, in which.

DETAILED DESCRIPTION

Figure 1:
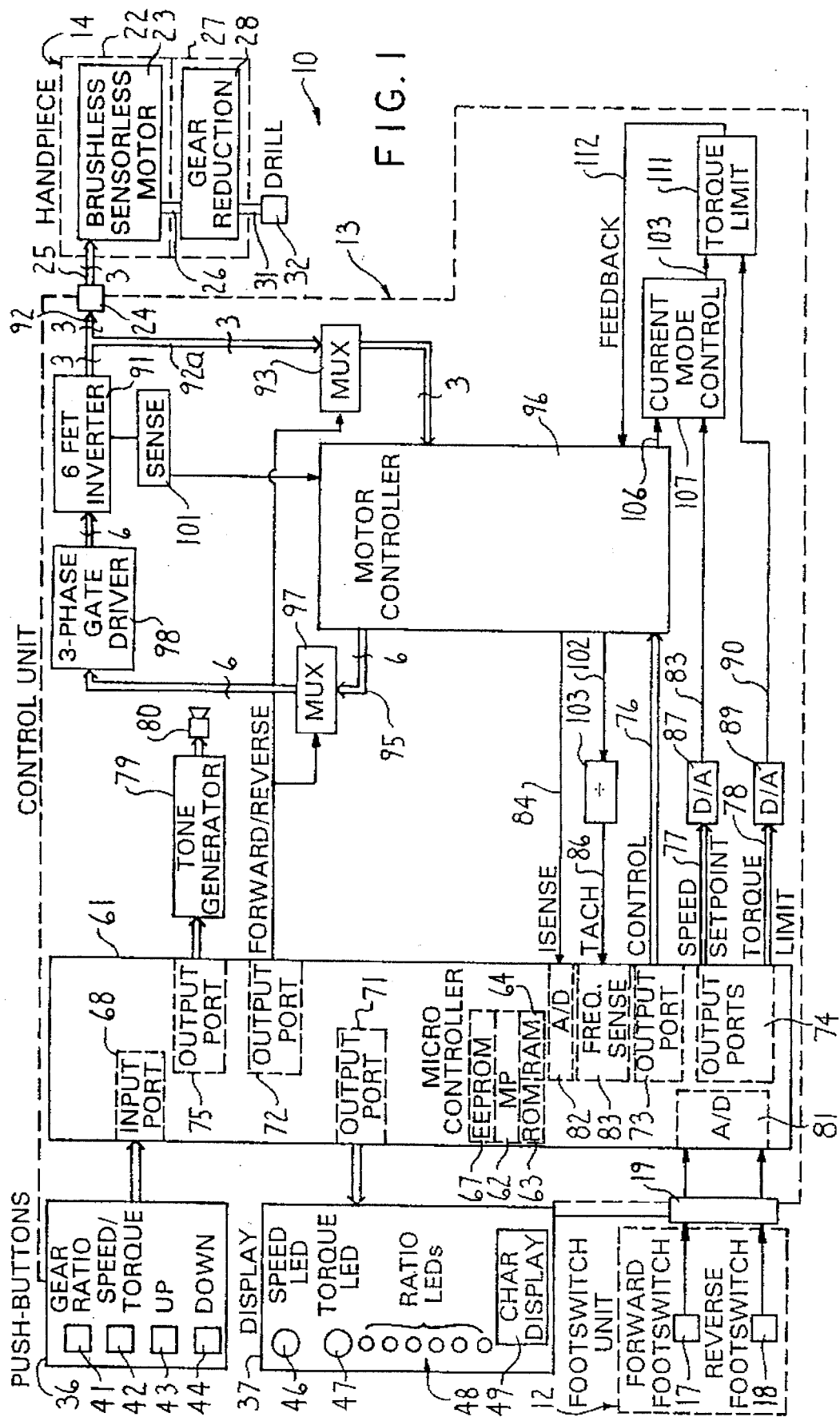
FIG. 1 is a block diagram of a dental drill system which embodies the present invention.

FIG. 1 shows a powered medical instrument 10 which is a dental drill system. The dental drill system 10 includes a foot switch unit 12 coupled to a control unit 13 which is in turn coupled to a handpiece 14.

The foot switch unit 12 includes a forward foot switch 17 and a reverse foot switch 18, each of which is detachably electrically coupled to the control unit 13 by a connector 19. The forward foot switch 17 and the reverse foot switch 18 can each manually be operated by a foot, and each produce an output voltage which progressively changes as the foot switch is progressively activated.

The handpiece 14 includes a motor portion 22 having therein a brushless sensorless three-phase AC electric motor 23 of conventional design. The motor 23 is detachably electrically coupled to the control unit 13 through a three-wire cable 25 and a connector 24. The motor has a rotatably supported shaft 26.

The handpiece 14 also includes a gear reduction portion 27 which is detachably coupled to the motor portion 22 and which includes a gear reduction mechanism 28. The gear reduction mechanism 28 is driven by the rotating motor shaft 26, and has an output shaft 31 that rotates at a slower speed than the motor shaft 26. The output shaft 31 has mounted on it a tool 32, which in FIG. 1 is a dental drill. There are actually six different gear reduction portions 27 which can be interchangeably coupled to the motor portion 14. The only difference between them is that each has a different gear reduction ratio, and therefore only one of the gear reduction portions 27 is illustrated in FIG. 1.

The control unit 13 includes a control panel which has a push-button section 36 and a display section 37. The push-button section 36 includes four push buttons, namely a GEAR RATIO push button 41, a SPEED/TORQUE push button 42, an UP push button 43, and a DOWN push button 44. The display section 37 includes several light emitting diodes (LEDs), including a SPEED LED 46, a TORQUE LED 47, and six RATIO LEDs 48. Each of the six RATIO LEDs 48 corresponds to the gear reduction ratio of a respective one of the six gear reduction portions 27. The display section 37 also includes a character display 49, which in the preferred embodiment is a conventional multi-digit LED display.

The control unit 13 also includes a microcontroller 61, which in the preferred embodiment is based on a conventional and commercially available microcontroller available from Signetics of Sunnyvale, Calif., as Part No. S80C552-AN68, and includes associated support circuitry. Those of ordinary skill in the art will recognize that the microcontroller 61 could also be based on other conventional and commercially available integrated circuits. The major components of the microcontroller 61 will be briefly described to facilitate a thorough understanding of the present invention, but those skilled in the art will readily recognize how to implement a suitable microcontroller. Therefore, and since the microcontroller 61 is not in and of itself the focus of the present invention, the microcontroller 61 is not described in extensive detail.

As shown in FIG. 1, the microcontroller 61 includes a microprocessor 62, which is coupled to a read only memory (ROM) 63 storing a program executed by the microprocessor 62, a random access memory (RAM) 64 where the microprocessor can store variables and other data utilized by its program, and an electrically erasable programmable read only memory (EEPROM) 67. The contents of the EEPROM 67 can be changed by the program in the RAM 63 but are retained through a power outage, and the EEPROM thus be used to store data which changes but which must be maintained when power is off.

The microcontroller 61 has an input port 68 which receives the output of each of the push-button switches 41–44. It also has an output port 71 which drives each of the elements 46–49 of the display, an output port 72 which produces a signal FORWARD/REVERSE indicating whether the motor 23 should rotate in a forward direction or a reverse direction, an output port 73 which outputs several motor control signals at 76, output ports 74 which output a multi-bit digital speed setpoint at 77 and a multi-bit torque limit value at 78, and an output port 75 which controls a conventional tone generator 79 that can produce audible beeps through a small loudspeaker 80.

The microcontroller 61 also includes an analog-to-digital (A/D) converter 81 that receives the analog output voltages from each of the foot switches 17 and 18 and converts each to a digital value, and an A/D converter 82 that receives on a line 84 a signal ISENSE, which is an analog voltage having a magnitude corresponding to the prevailing magnitude of the motor current, the A/D converter 82 converting the analog voltage of the ISENSE signal into a digital value. The microcontroller 61 also has a frequency sensing circuit 83 that receives a TACH signal on line 86. The TACH signal on line 86 is a square wave pulse of 50% duty cycle, the frequency of the TACH signal representing the present speed of the motor 23. The frequency sensing circuit 83 detects a leading edge of the TACH signal, measures the time until a trailing edge occurs, and stores the measured time interval in a predetermined location of the RAM 64 for subsequent use by the processor, as described later.

The digital speed setpoint value 77 from the output port 74 is coupled to a conventional digital-to-analog (D/A) converter 87, which converts the digital value into an analog signal on line 88 that has a voltage corresponding in magnitude to the magnitude of the digital value at 77. Similarly, the digital torque limit value 78 is supplied to a D/A converter 89, which outputs a torque limit signal 90 with a voltage corresponding in magnitude to the magnitude of the digital torque limit value 78.

The control unit 13 includes a six FET invertor, which is a conventional circuit having three pairs of FETs, each pair being arranged in a totem pole configuration between a DC voltage and ground. The node between the transistors of each totem pole pair is connected to the motor 23 through the connector 24 by a respective one of three conductors 92. The transistors of each totem pole pair are switched in a complementary manner, so that the node between the transistors of each pair alternates between the DC voltage and ground so as to generate AC square wave signals which are supplied to the motor 23 by lines 92 and 25 in order to commutate the motor windings 23 in a manner causing the motor shaft 26 to rotate.

The conductors 92 that extend between the inverter 91 and the motor controller 24 have a set of branch conductors 92a that are connected to a motor controller 96 through a multiplexer 93. The motor controller 96 outputs six switching control signals at 95 to a multiplexer 97, which then forwards them to a three-phase gate driver 98, which in turns supplies the six signals to the invertor 91, where each of the six signals is applied to the gate input of a respective FET. The motor controller 96 is based on a conventional and commercially available integrated circuit, which in the preferred embodiment is available from Micro Linear of San Jose, Calif., as Part No. ML4411. The motor controller 96 was designed primarily for applications such as operating the motor of a conventional hard disk drive in a computer system, where the motor runs at a constant speed, and in such a conventional application the six output lines 95 of the motor controller 96 are directly connected to the gates of respective FETs in a conventional invertor of the type shown at 91.

However, the motor for a computer hard disk drive is relatively small in comparison to the motor 23 utilized in the preferred embodiment, as a result of which the six FETs in the invertor 91 must be components capable of handling a larger amount of current than the components in a motor for a disk drive, which in turn means that the amount of current required to control switching of the FETs in the invertor 91 is more than the motor controller 96 is designed to output at 95. Accordingly, the three-phase gate driver circuit 98 is provided to amplify or boost the driving power of these six signals, so that they can comfortably drive the six FETs of the invertor 91. The three-phase gate driver circuit 98 is also conventional, and in the preferred embodiment is an IR2130 chip available commercially from International Rectifier of El Segundo, Calif.

The motor controller 96 is designed to run a motor in only one rotational direction. The multiplexers 93 and 97 are provided so that the control unit 13 can selectively control the motor 23 for both forward and reverse operation. In particular, the multiplexers 93 and 97 each supply all input signals directly to corresponding output lines when the microcontroller 61 has set the FORWARD/REVERSE line to select forward operation, and swap selected signals between the multiplexer inputs and multiplexer outputs when the microcontroller 61 sets the FORWARD/REVERSE line to select reverse operation. Thus, the motor controller 96 thinks that it is always operating the motor 23 in a forward direction, whereas in fact the motor is operated in either a forward or reverse direction in dependence on how the multiplexers 93 and 97 are currently controlled by the FORWARD/REVERSE line from microcontroller 61.

A conventional current sensing circuit 101 is coupled to the invertor at 91, and provides to the motor controller 96 a signal representative of the amount of current flowing through the invertor 91, which in turn corresponds to the amount of current flowing through motor 23. The motor controller 96 then outputs on line 84 the ISENSE signal, which is based on the output of sense circuit 101 and which is an analog voltage having a magnitude representing the magnitude of the motor current, the magnitude of the motor current being, in turn, proportional to motor torque. The motor controller 96 also outputs a square wave signal on line 102 which has a 50% duty cycle and which has a frequency corresponding to the magnitude of the rotational speed of the motor 23. In particular, the frequency increases and decreases as the speed increases and decreases. The frequency of the signal on line 102 is divided down by a conventional frequency divider circuit 103, the output of the circuit 103 being the TACH signal supplied on line 86 to the frequency sensing circuit 83.

The motor controller 96 generates at 106 an analog signal having a voltage representing actual motor speed by monitoring the back EMF pulses generated by the motor and transmitted through cable 25, connector 24 and conductors 92 and 92a. A current mode control circuit 107, which is described in more detail later with reference to FIG. 2, receives the analog actual speed signal 106 from motor controller 96 and the analog speed setpoint signal 88 from D/A converter 87, and produces an output 108 which is coupled to one input of a torque limit circuit 111, the other input of torque limit circuit 111 being coupled to the analog torque limit value produced on line 90 by the D/A converter 89. The output of the torque limit circuit 111 is a FEEDBACK signal 112, which is coupled to an input of the motor controller 96.

Figure 2:
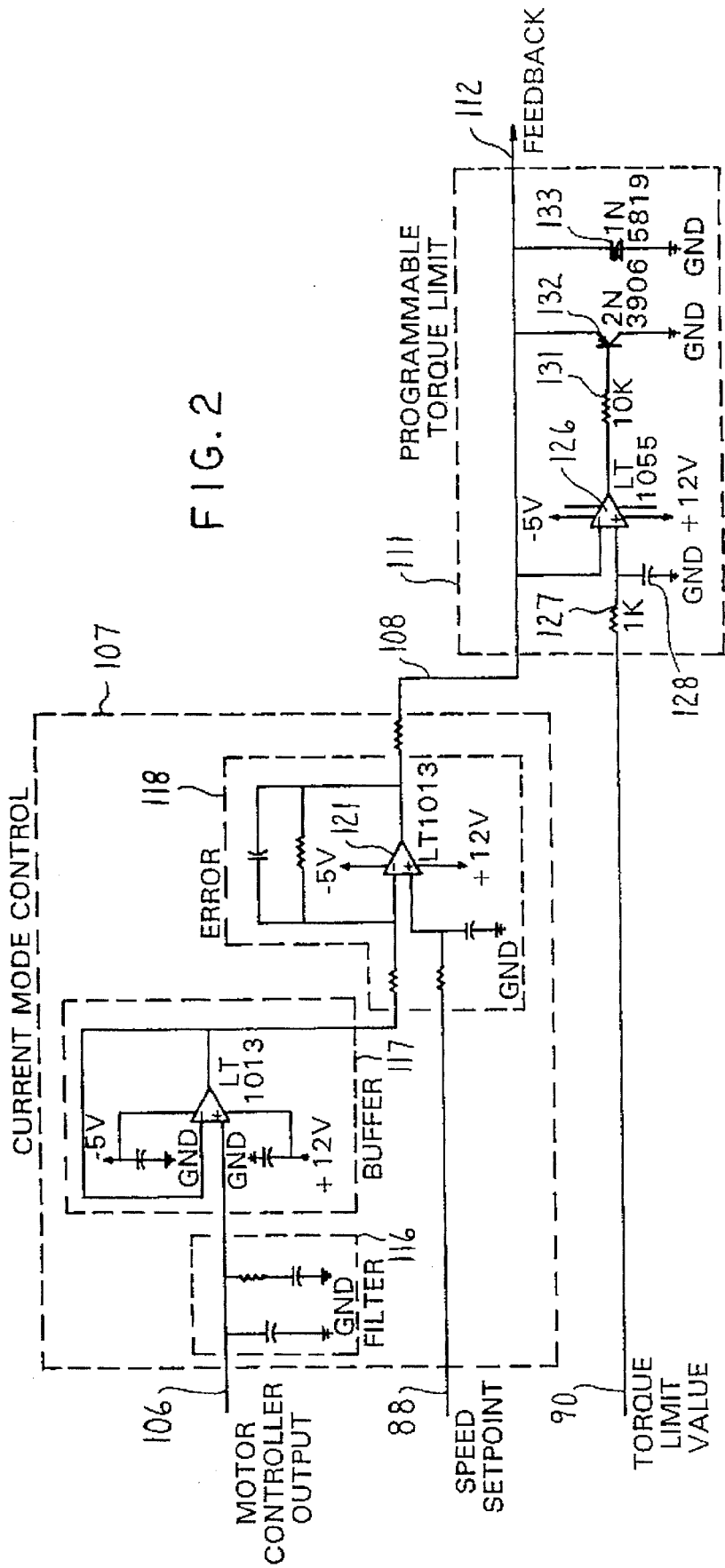
FIG. 2 is a circuit schematic for a portion of the system of FIG. 1.

The current mode control circuit 107 and torque limit circuit 111 are shown in more detail in FIG. 2. The current mode control circuit 107 is itself substantially conventional, and in a conventional system the output 108 of the current mode control circuit would be connected directly back to the FEEDBACK input of the motor controller 96. The current mode control circuit 107 includes a filter section 116 which filters the actual speed signal 106 from the motor controller 96, a buffer section 117 which amplifies the output of the filter section 116, and an error section 118 which has a differential error amplifier 121. The error amplifier 121 compares the filtered and buffered version of signal 106 to the speed setpoint signal 88 from the microcontroller 61, and generates at 108 an output signal which represents the magnitude of the difference between the motor controller output 106 and the speed setpoint 88. The speed setpoint 88 is an analog voltage representing a desired or target speed for the motor. If the motor is running at the desired speed, then the inputs to the error amplifier 121 will have approximately the same voltage, and the output of the error amplifier 121 will be stable and at a voltage level causing the motor to run at the appropriate speed. On the other hand, if the actual speed deviates from the target speed, the error amplifier 121 will increase or decrease its output voltage level by an amount corresponding to the deviation of the actual motor speed from the target motor speed.

In a conventional system, the torque limit circuit 111 would not be present, and the error signal 108 would be connected directly back to the FEEDBACK input of the motor controller 96. Depending on the sign and magnitude of the FEEDBACK signal, the motor controller 96 increases and decreases the widths of the pulses output at 95 to control the invertor 91. As is known by those of ordinary skill in the motor control art, this pulse width modulation (PWM) has the effect of varying the amount of current supplied to the motor, in particular by respectively increasing and decreasing the amount of current supplied to the motor as the pulse widths increase and decrease. The motor torque necessarily increases and decreases as the amount of current supplied to it increases and decreases, thereby causing the motor to tend to speed up or slow down.

If the dental drill 32 is engaging a tooth and applying a load to the motor, the motor will tend to slow down from its target speed, as a result of which the error amplifier 121 will produce an output voltage with a magnitude indicating that current to the motor should be increased in order to increase torque and return the motor to the target speed. However, a typical motor 23 will have the capability to produce significantly more torque than certain components in the drive train can withstand, and it is thus desirable to limit the motor torque in order to avoid breaking these drive train components. Limiting the torque, of course, would mean that the motor would not be generating enough torque to rotate the motor shaft to its target speed, and thus the motor would continue to run at a speed less than the target speed, or would progressively slow down.

A further consideration is that, depending on the particular gear reduction portion 27 which happens to be attached to the motor portion 22, different levels of torque limiting are appropriate. In order to allow different levels of torque limiting, the programmable torque limit circuit 111 (FIG. 2) is provided. The torque limit circuit 111 includes an operational amplifier 126, which has JFET inputs. In the preferred embodiment, the operational amplifier 126 is an LT1055 commercially available from Linear Technology Corporation of Milpitas, Calif. The error signal 108 from the current mode control circuit 107 is connected directly to the output 112 and to the negative input of the operational amplifier 126. The torque limit signal 90 from the D/A circuit 89 and microcontroller 61 is connected through a resistor 127 to the positive input of the operational amplifier 126, the positive input also being connected through a capacitor 128 to ground. The output of the operational amplifier 126 is connected through a resistor 131 to the base of a transistor 132, which has an emitter connected to the signals 108 and 112, and a collector connected to ground. The transistor 132 is selected so that it always operates in a linear mode, and in the preferred embodiment is a 2N3906. A Schottky diode 133 has its cathode and anode respectively connected to the emitter and collector of the transistor 132.

When the voltage of the error signal 108 has a magnitude indicating that motor torque should be increased, the operational amplifier 126 compares the error signal to the torque limit value 90. So long as the error signal does not exceed the torque limit value 90, the error signal is forwarded without change to the motor controller 96, which in turn uses PWM to increase the motor current and thus the motor torque in order to speed the motor back up to its setpoint speed. On the other hand, if the operational amplifier 126 determines that the error signal 108 has a magnitude which exceeds the torque limit value 90, the operational amplifier 126 turns on the transistor 132 in order to clamp or limit the magnitude of the signal at 108 to a value corresponding to the torque limit value. Thus, even if the error amplifier 121 is outputting a voltage of greater magnitude, the transistor 132 will limit the magnitude of the error signal at 108 so that the PWM carried out by the motor controller 96 is limited in a manner which in turn limits the current supplied to motor 23, and thus the torque of motor 23. As the motor continues to slow down, the error amplifier 121 will increase the magnitude of its output, but the torque limit circuit 111 will keep the signal 112 clamped at the magnitude corresponding to torque limit value 90, and thus the motor torque will be limited to a value which avoids breakage of drive train components. The microcontroller 61 can, of course, selectively change the torque limit value 90, causing the programmable torque limit circuit 111 to change the magnitude at which the error signal 108 is clamped and thus change the maximum torque permitted for motor 23.

Figure 3:
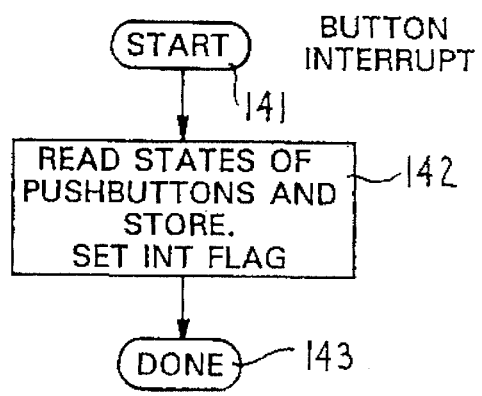
FIG. 3 is a flowchart of an interrupt routine which is executed by a microprocessor in the system of FIG. 1 when a button is pressed on a control panel.
Figure 4:
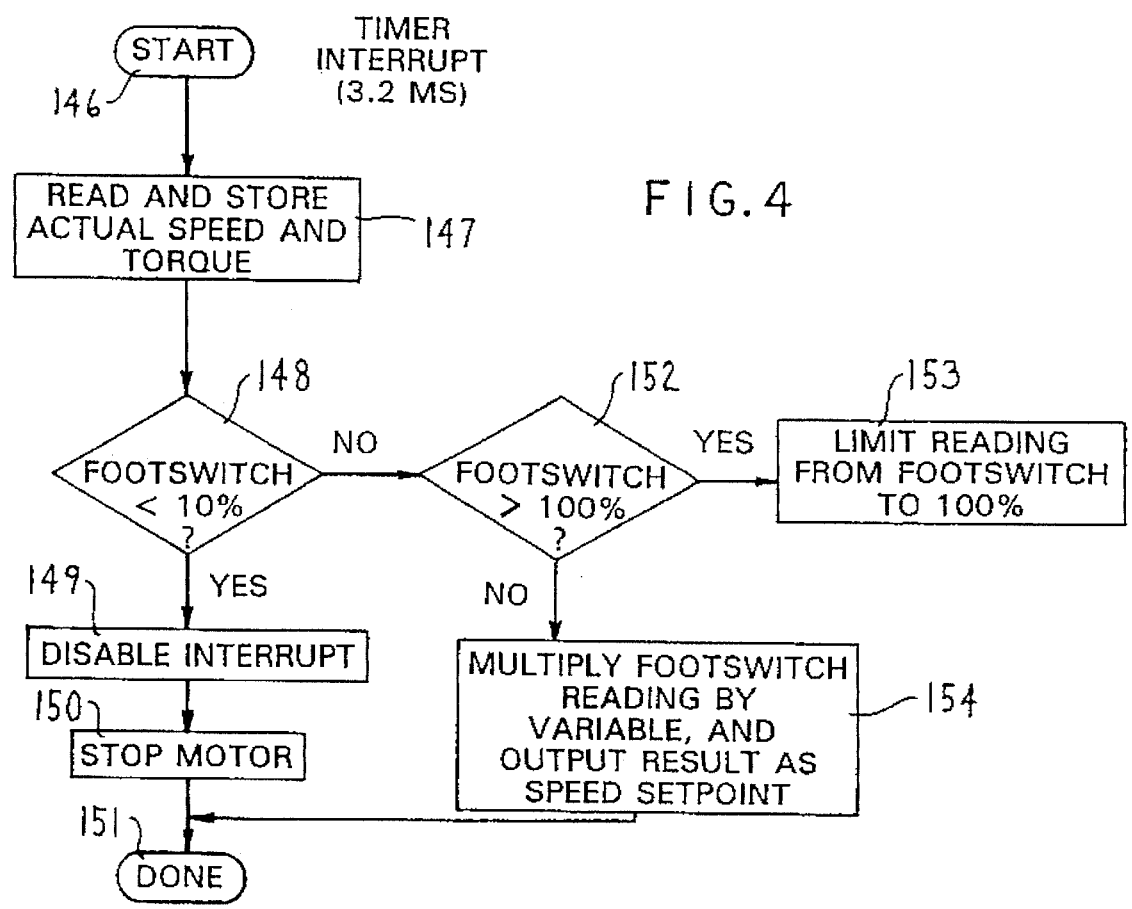
FIG. 4 is a flowchart of a further interrupt routine which is executed by the microprocessor at periodic intervals.
Figure 5A:
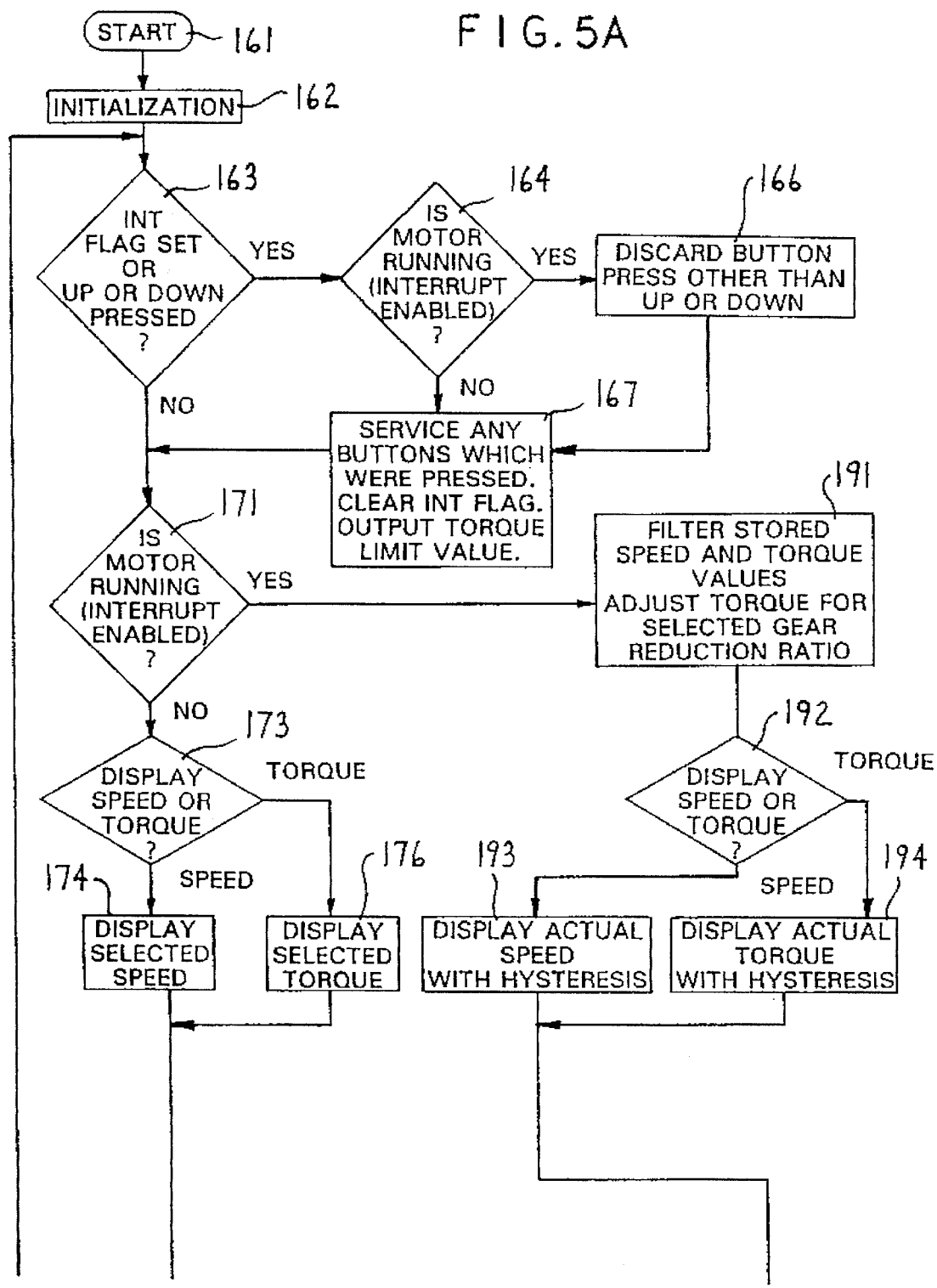
FIG. 5 is a flowchart of a main routine executed by the microprocessor.
Figure 5B:
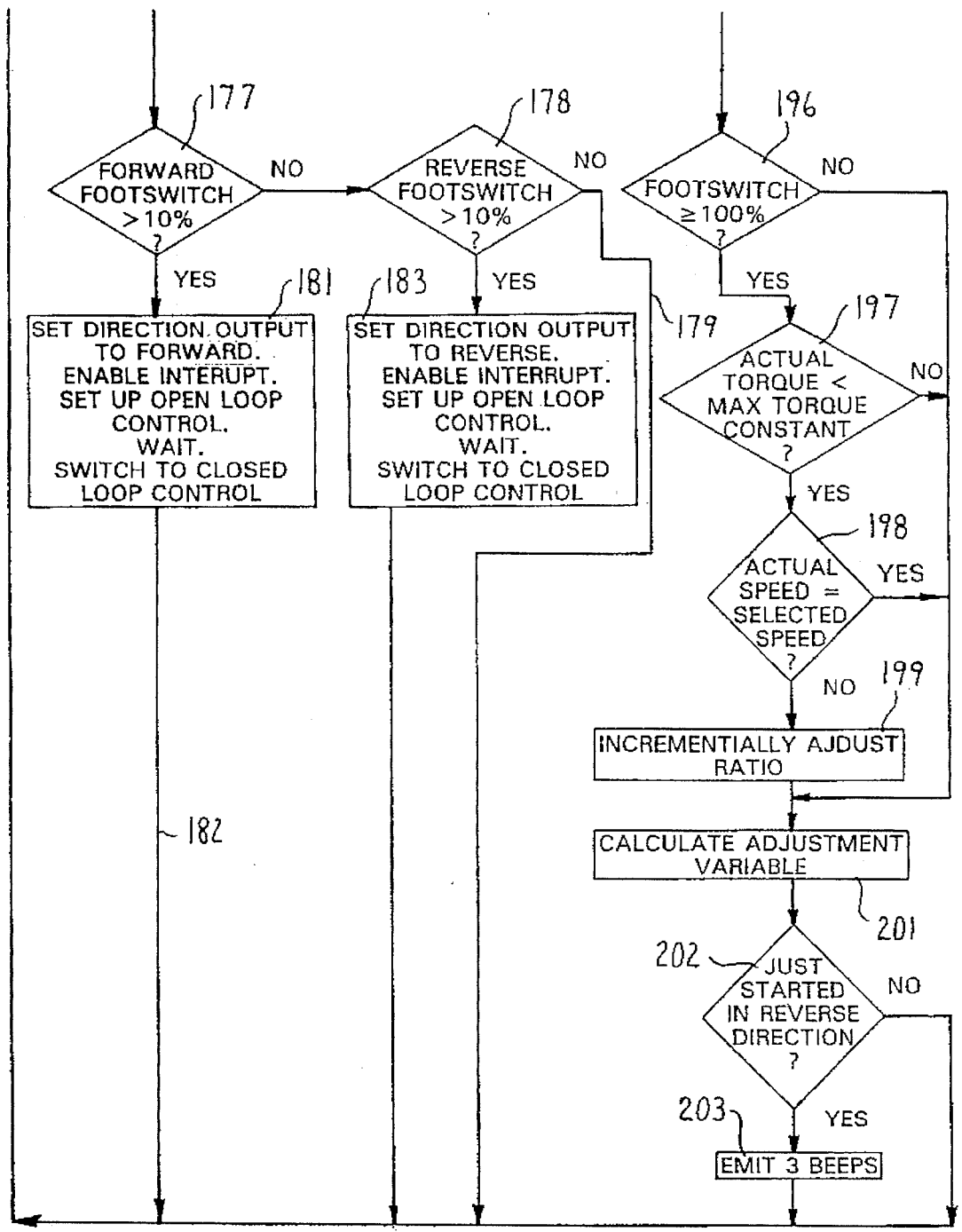

Before explaining the flowcharts of FIGS. 3 to 5 in detail, it will be helpful to provide an overview of one aspect of system operation. More specifically, the foot switches 17 and 18 each output an analog voltage that progressively changes from an initial value to a maximum value as the foot switch is progressively manually actuated. The maximum value may vary somewhat from foot switch to foot switch as a result of component tolerances, and a predetermined constant output somewhat less than the typical maximum output value is therefore selected to represent 100% actuation of the foot switch. Depending on its tolerances, a foot switch will usually be capable of producing a maximum output value which exceeds the arbitrary 100% value, and which may for example be 115% of the predetermined constant output for one foot switch, 125% for another, and so forth.

Further, as mentioned above, an operator can use the UP and DOWN push buttons 43 and 44 to specify a maximum motor speed, up to 40,000 rpm. If the operator selects a maximum motor speed of 30,000 rpm, then when the operator fully depresses one of the foot switches, the operator expects that the digital display 49 will show the actual motor speed as precisely 30,000 rpm. Those skilled in the art will recognize that various system components have manufacturing tolerances which, in a conventional system, would cause the motor 23 to run at a speed slightly above or slightly below the preferred value of 30,000 rpm. For example, the maximum output from any foot switch may vary from one foot switch to another (as discussed above), the components used within the current mode control circuit 107 controlling motor speed will have small variations from part to part as a result of manufacturing tolerances, and the speed constant of the motor 23 (a function of manufacturing tolerances) may vary from motor to motor by more than 10%. These effects could in theory be reduced to some extent by purchasing only components manufactured to strict tolerances, but such components would be significantly more expensive, and would still not entirely eliminate the problem. The present invention includes an approach which permits use of relatively inexpensive components manufactured to relatively loose tolerances, while ensuring that full actuation of the foot switch causes operation of the motor 23 at substantially precisely the maximum speed selected by the user, in particular to within 0.05% of the maximum speed selected by the user.

In general terms, and as previously discussed, a foot switch output with a magnitude in excess of the arbitrary 100% value is limited within the processor to the 100% value in order to eliminate the effect of variations in actual maximum output from one foot switch to another. The processor 62 then adjusts the foot switch output using a function, which is described below, and outputs the result to the speed setpoint lines 77 through output ports 74.

When the processor detects that the foot switch is fully actuated, or in other words has an output at or above the 100% level, then it is desirable that the motor 23 be running at a speed which is exactly the maximum speed selected by the user, and the processor therefore compares the user-selected speed to the actual speed determined using TACH signal 86. In this regard, it is important to note that the entire speed feedback path from the motor controller 96 to D/A converter 87 through line 102, frequency divider 103, line 108, frequency sensing circuit 83 and micro controller 61 is digital, and thus highly accurate. If the processor determines that the actual motor speed is not substantially exactly the user-selected speed, the processor adjusts the function used between the output of foot switch unit 12 and speed setpoint lines 77, until the motor 23 is in fact running substantially precisely at the user-selected speed. Stated differently, the function is dynamically adjusted to compensate for manufacturing tolerances which may be present in various system components.

If the operator reduces the pressure on the foot switch in order to slow the motor down, then after the foot switch output drops below the 100% value, the processor continues to use the adjusted function but without making any further adjustments until such time as the foot switch output is again at or above 100%.

With respect to adjustment of the function, there is one further factor which must be taken into account. In particular, in a situation where the motor is operating at a specified maximum torque and the torque limiting circuit 111 is preventing any increase in motor torque, the motor 23 needs to compensate by reducing its speed regardless of whether the foot switch is fully depressed. Therefore, even if the foot switch output is at or above the 100% level, the function is not adjusted unless the actual motor torque is less than a predetermined maximum torque constant (which does not change).

One specific function which is used in the preferred embodiment is represented by the following equations:

$$SSP = FSO \times VARIABLE \quad (1)$$

$$VARIABLE = CSP \times \frac{MMS}{40K} \times RATIO \quad (2)$$

In these equations, FSO represents the foot switch output from 10% to 100% in the form of a fraction from 0.1 to 1.0, VARIABLE is a number representing the function itself, and SSP is the speed setpoint value output on lines 77. The value VARIABLE is the product of a predetermined constant setpoint CSP (which if output at 77 would cause the motor 23 to run at approximately its highest allowable speed of 40,000 rpm), the user-selected maximum motor speed value MMS divided by the top allowable speed of 40,000 rpm, and a number called RATIO. The value of RATIO is set to an initial value of 1.0 each time the system is turned on, and is thereafter increased or decreased by the processor where necessary to adjust the function so that the actual maximum motor speed is substantially precisely the selected maximum motor speed MMS.

Turning now to the flowcharts, each time one of the push buttons 41–44 is pressed, the microprocessor 62 in the microcontroller 61 is interrupted, and executes the interrupt routine shown as a flowchart in FIG. 3. In particular, execution of the interrupt routine starts at 141, and at 142 the processor reads the states of all four push buttons 41–44 and stores these states in the RAM 64. Then, the processor sets a software interrupt flag in the RAM 64 to indicate that a push button has been pressed. The processor then returns to execution of the interrupted program at 143.

The microcontroller 61 also includes a hardware timer which interrupts the processor 62 every 3.2 milliseconds, and this interrupt is serviced by the interrupt routine shown as a flowchart in FIG. 4. The timer interrupt can be selectively enabled and disabled by the software. The software enables the timer interrupt when the motor 23 is running, and disables the timer interrupt when the motor 23 is off. Since the timer interrupt is enabled only if the motor is running, the routine of FIG. 4 is entered only if the motor is running, which necessarily means that the user has manually operated one of the foot switches 17 and 18.

Execution of the timer interrupt routine of FIG. 4 begins at block 146, and control proceeds to block 147, where the processor reads and stores the actual speed and torque of the running motor 23. In particular, and as mentioned above, the TACH signal 86 is a digital signal in the form of a square wave having a frequency which varies with the speed of motor 23. Due to the fact that the motor controller 96 uses PWM techniques to control motor speed through the inverter 91, the TACH signal 86 from the motor controller 96 is an extremely accurate indication of the precise actual speed of motor 23. As already explained, the frequency sensing circuit 83 measures the width of each pulse of the TACH signal 86, the pulse width varying directly with variations in frequency, and stores the measured pulse width in a location of the RAM 64 to serve as a value representing the actual speed of the motor. In the interrupt routine of FIG. 4, the processor 62 reads this value from the location in the RAM 64, and then stores the value in a different location of the RAM 64 (where it is not subject to further change by the frequency sensing circuit 83). The ISENSE signal 84 from the motor controller 96 is an analog voltage which represents the current presently being supplied to motor 23 and which thus also represents motor torque, and the A/D converter 82 provides a digital output representing the magnitude of this voltage. The processor reads this digital output from the A/D converter 82, and stores it in a location of the RAM 64 as an indication of the actual torque presently being generated by the motor 23.

Control then proceeds to block 148, where the processor checks the foot switch 17 or 18 which has been manually actuated in order to see if the magnitude of the output from it has dropped below 10% (or in other words one-tenth of the arbitrary 100% value). If less than 10%, then it is assumed that the user is taking his foot off the foot switch and that the motor is to be stopped, and so at block 149 the timer interrupt is disabled, which will prevent another entry to the interrupt routine of FIG. 4. Then, control proceeds to block 150, where the processor 62 sets the control lines 76 so as to instruct the motor controller 96 to stop the motor. Control then proceeds to block 151, where the processor returns to the program which was interrupted.

On the other hand, if it was determined at block 148 that the actuated foot switch is producing an output greater than or equal to the 10% level, then at block 152 a check is made to see if the foot switch output is greater than 100%. If above 100%, then at block 153 the processor internally limits the foot switch reading to the 100% value. In either case, the foot switch reading is multiplied in block 154 by the above-described quantity called VARIABLE which represents the function, and then the resulting value is output through output ports 74 to the line 77 in order to serve as the speed setpoint. The processor then returns to the interrupted program at block 151.

FIG. 5 is a flowchart of the main routine executed by the processor 62. When power to the system is first turned on, or in the case of a reset, the processor begins program execution at 161, and performs at block 162 some initialization of a conventional type, such as system diagnostics and set-up.

Following initialization, control proceeds to block 163, where the processor checks to see whether the interrupt flag is set or whether one of the UP and DOWN push buttons 43 and 44 has been pressed. As explained above, the interrupt flag is set by the routine of FIG. 3 whenever one of the four push buttons 41–44 is initially pressed. This will include the UP and DOWN push buttons 43 and 44 when either is first pressed, but as to these two buttons a user may hold one of them down in order to cause continuous scrolling through available selections of a parameter such as motor torque. Therefore, a separate check of these two push buttons is made in block 163 in case one is still pressed even after its initial actuation was detected and serviced by setting of the interrupt flag. If it is determined at block 163 that any button is pressed and needs to be serviced, then control proceeds to block 164, where the processor checks to see whether the motor is running, in particular by checking to see whether the timer interrupt (associated with the interrupt routine of FIG. 4) is enabled. If the motor is running, then push buttons other than the UP and DOWN buttons 43 and 44 are ignored, and in particular any indication that the GEAR RATIO button 41 or SPEED/TORQUE button 42 has been pressed is discarded at 166. From block 166, or from block 164 if the motor is not running, control proceeds to block 167. In block 167, the processor services any push-button operation which has occurred and which was not discarded at block 166.

More specifically, the character display 49 of the control unit can display the speed of the motor or the torque of the motor, but can only display one of them at any given time. Accordingly, the SPEED/TORQUE push button 42 is used to toggle between display of speed and display of torque. In particular, in a situation where torque is presently selected, the processor keeps the TORQUE LED 47 lit, and displays a torque value in the character display 49 in a manner described later. If the operator then presses the SPEED/TORQUE push button 42, the processor 61 turns off the TORQUE LED 47 and turns on the SPEED LED 46, and will display a speed value in the character display 49 in a manner described later. If the SPEED/TORQUE push button 42 is pressed again, the processor will revert to the state where torque is displayed. When the motor is not running, the character display 49 is used to display a maximum motor speed or a maximum motor torque, whereas if the motor is running the display 49 is used to display actual motor speed or actual motor torque, as will be described later.

As previously mentioned, the system 10 includes six interchangeable gear reduction portions 27, each having a different gear ratio. The six ratio LEDs 48 on the display each correspond to a respective gear ratio, and one of the LEDs 48 representing the gear ratio of the gear reduction portion 27 currently installed on the handpiece is normally illuminated. If the operator replaces the gear reduction portion 27 with another gear reduction portion having a different ratio, the operator presses the GEAR RATIO push button 41. Each time the GEAR RATIO push button 41 is pressed, the processor 62 turns off one of the LEDs which had been lit and illuminates the next successive LED 48, and records in the RAM 64 a number representing the ratio associated with the newly-lit LED. By pressing the GEAR RATIO push button 41 one or more times, the operator ultimately lights the LED 48 corresponding to the ratio of the gear reduction portion 27 currently installed on the handpiece. Each of the LEDs 48 has next to it a label indicating the associated gear ratio, but these labels have been omitted in FIG. 1 for clarity and because the invention is not limited to any particular ratio values.

Each of the six gear ratios has associated with it a set of predetermined maximum torque values from which the user can select. The maximum torque values in each set typically differ from those in other sets. When the user has selected torque for display on the character display 49, and when the motor is not running, the processor 62 will display the currently-selected maximum torque value for the selected gear ratio. If the operator repeatedly presses the UP or DOWN push button 43 or 44, the processor will cycle through the available selections by successively displaying them, and the last selected maximum torque value for the current gear ratio is stored in the RAM 64, and is output through output ports 74 to the lines 78 to serve as the torque limit value supplied through D/A converter 89 to the torque limit circuit 111.

If motor speed is selected for display then the UP and DOWN push buttons are used to change the user-selected maximum motor speed, whereas if torque is selected for display they are used to change the user-selected maximum motor torque. More specifically, if speed is selected and one of the UP and DOWN push buttons is pressed, then the maximum speed is incremented or decremented by a specific amount when the block 167 is executed. If the button is pressed and held, then the maximum speed is incremented or decremented by the specific amount each time block 167 is executed while the button is held. However, the UP and DOWN push buttons 43 and 44 are not permitted to increment or decrement the maximum motor speed beyond certain values representing physical limitations of the system components. For example, the fastest speed at which the system will operate the motor 23 is the speed of 40,000 rpm, and the processor 62 will therefore not permit the user to increment the maximum motor speed above 40,000 rpm. The user can, of course, select a maximum motor speed which is less than 40,000 rpm.

If torque is selected, the processor selects the next successive value in the current set each time one of the UP and DOWN push buttons is pressed. If the button is pressed and held, the processor scrolls successively through the torque values in the current set, in particular by periodically scrolling to the next torque value during a succession of executions of block 167 while the UP or DOWN button is held.

The maximum motor speed and maximum motor torque values selected by the user are stored in the RAM 64, and the maximum torque value is also output through output port 74 to lines 78 to serve as the torque limit value supplied through D/A converter 89 to torque limit circuit 111. In block 167, the processor also clears the interrupt flag which was set in block 142 of FIG. 3, to reflect the fact that it has serviced the button or buttons which resulted in setting of the flag.

From block 167, and from block 163 if the interrupt flag was not set and the UP and DOWN buttons were not pressed, control proceeds to block 171. In block 171, the processor checks to see if the motor is running, in particular by checking to whether the timer interrupt is enabled in the same manner as in block 164. If the timer interrupt is not enabled, control proceeds to block 173, where the processor checks to see whether the user has indicated that the character display 49 is to be used to display speed or torque. If the user has selected speed for display, then at block 174 the processor outputs to the character display 49 the maximum motor speed, which the user selects in the manner described above in association with block 167. Alternatively, if the user has selected torque for display, then the processor outputs to the character display 49 the maximum motor torque, which the user selects in the manner described above in association with block 167. In either case, control then proceeds to block 177.

In blocks 177 and 178, the processor essentially checks to see whether either of the foot switches 17 and 18 has been manually actuated by an amount sufficient to justify restarting the motor 23. In particular, at block 177 the processor checks to see whether the forward foot switch is producing an output representing at least 10% actuation, and at block 178 checks to see whether the reverse foot switch 18 is producing an output representing at least 10% actuation. If neither foot switch is actuated by at least 10%, control proceeds through each of blocks 177 and 178 and then returns at 179 to block 163. So long as the motor is stopped, the processor will repeatedly execute a loop which includes blocks 171–178.

Eventually, the user will press one of the foot switches in order to start the motor, and for purposes of example it will be assumed that the user presses the forward foot switch. The first time thereafter that the processor reaches block 177, the processor will detect that the forward foot switch is more than 10% actuated, and will proceed to block 181, where it records an internal indication in the RAM 64 that the motor is to be operated in a forward direction, and then uses output port 72 to output a voltage level on the FORWARD/REVERSE line which causes the multiplexers 93 and 97 to select forward motor rotation. Then, the processor enables the timer interrupt so that periodic execution of the interrupt routine of FIG. 4 will resume. Since the motor presently has a speed of 0 rpm, closed loop control of the motor based on feedback of the actual motor speed is not practical until the motor is actually rotating at some relatively low speed, and the processor therefore uses the control lines 76 to instruct the motor controller 96 to carry out open loop control of the motor in a manner intended to cause the motor to start rotating, The manner in which this is carried out is conventional and not itself a part of the present invention, and is therefore not described in detail. The processor then waits a predetermined period of time during which the motor shaft should begin to rotate and should reach substantially the speed at which closed loop control can be utilized, at which point the processor adjusts control lines 76 to instruct the motor controller 96 to switch to closed loop control, where the signals received through multiplexer 93 and on FEEDBACK line 112 are taken into account in formulating control signals for the invertor 91. Control then returns at 182 to block 163.

If the operator had operated the reverse foot switch rather than the forward foot switch, control would have proceeded through blocks 177 and 178 to block 183, where the processor would carry out essentially the same sequence of activity as in block 181, except that the FORWARD/REVERSE output would be set to an opposite logic level to cause the multiplexers 93 and 97 to effect motor rotation in a reverse direction.

After control is returned to block 163 from either of blocks 181 and 183, and then eventually reaches block 171 again, it will be determined in block 171 that the motor is now running (because the timer interrupt has been enabled), and control will proceed to block 191 rather than block 172. In block 191, the processor retrieves from the RAM 64 the speed and torque values which were stored in block 147 of FIG. 4, and then carries out software filtering using conventional techniques which are not pertinent to the present invention. The torque value is also adjusted by the selected gear ratio, to compensate for the effects of the gear reduction portion 27. Control then proceeds to block 192, where the processor checks to see whether the user has selected speed or torque for display. If speed is selected, the actual motor speed as determined from the TACH signal 86 (FIG. 1) is displayed on character display 49 at block 193, whereas if torque is selected, the actual torque as determined from the ISENSE signal 84 and as adjusted for the selected gear reduction ratio is displayed on the character display 49. The software implements a small amount of hysteresis in displaying actual speed or actual torque, in order to avoid flickering of the display. For example, if the actual speed was between 29,999 RPM and 30,000 RPM, and speed readings were alternating rapidly between these two values, the character display 49 would be an unreadable blur. Therefore, the software will continue to display a given value of actual speed even if the measured speed changes very slightly from the given value, and only if the measured actual speed changes from the displayed actual speed by a predetermined small amount will the processor update the display with the newly-measured actual speed. Hysteresis for the actual torque is handled in a similar manner.

From each of blocks 193 and 194, control proceeds to block 196. Blocks 196–199 represent the logic involved with deciding whether the function needs to be adjusted in order to bring actual motor speed into conformity with the user-selected maximum speed in the manner broadly outlined above. In particular, at block 196, the processor checks to see if the active foot switch has an actuation level at or above 100%. If not, then the motor is not supposed to be running at its maximum speed and no adjustment is necessary, so blocks 197–199 are skipped. Otherwise, the processor proceeds to block 197, where it checks to see if actual torque is less than the predetermined maximum torque constant. If actual torque is at the maximum level, then in order to facilitate torque limiting the actual speed should be allowed to drop below the specified maximum speed despite the fact that the foot switch is fully actuated. Accordingly, blocks 198 and 199 are skipped. On the other hand, if it is found that actual torque is less than the maximum torque constant, the processor proceeds to block 198 where it checks to see if the actual speed is equal to the user-selected maximum speed. If the speeds are effectively equal, then there is no need to adjust the function, and block 199 is skipped. Otherwise, the processor proceeds to block 199, where it either increments or decrements the value of RATIO, as appropriate to adjust the function in a manner bringing actual speed into conformity with the users-elected speed. Each time the processor executes the main loop and reaches block 199, the value of RATIO will be incremented or decremented by a small preset amount, until it is found at block 198 that actual speed has in fact been conformed to the user-selected speed, at which point block 199 will be skipped and RATIO will be maintained at the value which causes actual speed to conform to the user-selected speed.

Control ultimately reaches block 201, where the processor actually calculates the current value of the function, or in other words the current value of VARIABLE, according to the mathematical equation (2) set forth above. The resulting value of VARIABLE is stored in the RAM 64 for later use. In particular, and with reference to the foregoing discussion of FIG. 4, the next time the timer interrupt occurs and causes execution of the interrupt routine of FIG. 4, at block 154 the processor will multiply the foot switch reading by the value of VARIABLE according to the mathematical equation (1) set forth above, and output the result on line 77 as the speed setpoint.

From block 201 in FIG. 5, control proceeds to block 202, where the processor checks to see if operation of the motor in a reverse direction has just started. If so, then at 203 the processor uses output port 75, tone generator 79 and speaker 80 to generate three short beeps, in order to ensure that the operator realizes the motor is rotating in a reverse direction. When the motor is operating in a forward direction, or when it is operating in a reverse direction but the three beeps have already been emitted, block 203 is skipped. In any case, control ultimately returns to the beginning of the main loop at block 163.

Although a single preferred embodiment of the invention has been disclosed in detail for illustrative purposes, it will be recognized that there are variations and modifications of the disclosed apparatus which lie within the scope of the present invention.

The embodiments of the invention in which an exclusive property or privilege is claimed are defined as follows:

1. A medical instrument including:
   a tool;
   a brushless motor coupled to said tool for driving said tool through a selective repetitive path of movement at a selected speed, said motor being actuated in response to an application of a pulse width modulated signal thereto and developing a torque in response to the movement of said tool; and
   a control unit connected to said motor for applying said pulse width modulated signal thereto, said control unit including:
      a driver for generating a variable frequency pulse width modulated signal for application to said motor, said driver frequency modulating said pulse width modulated signal in response to a driver control signal applied to said driver wherein, said pulse width modulated signal has a current that varies with said torque developed by said motor;
      a speed sensor connected to said motor for monitoring said speed of said motor and producing a motor speed signal representative of said motor speed;
      a current sensor connected to said driver for producing a current signal representative of said torque developed by said motor;
      a speed controller connected to said speed sensor for receiving said speed signal, said speed controller being configured to compare said speed signal to a speed setpoint signal representative of a selected motor speed and to produce a speed error signal based on said comparison;
      a torque controller connected to said speed controller for receiving said speed error signal, said torque controller being configured to compare said speed error signal to a torque limit signal representative of a selected maximum torque and to produce a selectively adjusted speed error signal in response to said comparison; and
      a driver controller connected to said current sensor for receiving said current signal, to said torque controller for receiving said adjusted speed error signal and to said driver, said driver controller being configured to compare said current signal with said adjusted speed error signal, to produce said driver control signal based on said comparison and to transmit said driver control signal to said driver.

2. The medical instrument of claim 1, wherein said driver includes at least one transistor for periodically connecting said motor between a voltage source and ground and said current sensor is connected to said at least one transistor for monitoring the current therethrough.

3. The medical instrument of claim 2, wherein said torque controller is configured to selectively attenuate said speed error signal to produce said adjusted speed error signal when said speed error signal exceeds said torque limit signal.

4. The medical instrument of claim 1, wherein said motor is a multi-phase motor to which at least two pulse width modulation signals are applied and said driver produces a plurality of pulse width modulated signals for application to said motor.

5. The medical instrument of claim 4, wherein: said driver includes a plurality of inverters, each said invertor producing one of said pulse width modulated signals for application to said motor and each said invertor includes at least one transistor for periodically connecting said motor between a voltage source and ground; and said current sensor is connected to said invertors for monitoring current through said transistors.

6. The medical instrument of claim 5, further including:
   a gear reduction unit for coupling said tool to said motor, said gear reduction unit being configured to establish one of a plurality of reduction ratios between said motor and said tool so that said tool is actuated at a speed relative to said speed of said motor that is representative of a selected said reduction ratio; and
   an instrument controller connected to said gear reduction unit for establishing said selected gear reduction ratio in response to a user selection and said instrument controller being further configured to generate said torque limit signal as a function of the user-selected reduction ratio and to transmit said torque limit signal to said torque controller.

7. The medical instrument of claim 5, wherein said tool has a longitudinal axis and said motor is coupled to said tool so as to rotate said tool along said longitudinal axis.

8. The medical instrument of claim 7, wherein said tool is a drill.

9. The medical instrument of claim 1, further including:
   a gear reduction unit for coupling said tool to said motor, said gear reduction unit being configured to establish one of a plurality of gear reduction ratios between said motor and said tool so that said tool is actuated at a speed relative to said speed of said motor that is representative of a selected said gear reduction ratio; and
   an instrument controller connected to said gear reduction unit for establishing said selected gear reduction ratio in response to a user selection and said instrument controller being further configured to generate said torque limit signal as a function of the user-selected gear reduction ratio and to transmit said torque limit signal to said torque controller.

10. The medical instrument of claim 1, wherein said torque controller is configured to selectively attenuate said speed error signal to produce said adjusted speed error signal when said speed error signal exceeds said torque limit signal.

11. The medical instrument of claim 1, wherein said tool has a longitudinal axis and said motor is coupled to said tool so as to rotate said tool along said longitudinal axis.

12. The medical instrument of claim 11, wherein said tool is a drill.

13. The medical instrument of claim 1, wherein said current signal produced by said current sensor and applied to said driver controller is a variable voltage signal.

14. A medical instrument including:
    a tool;
    a brushless motor coupled to said tool for driving said tool through a repetitive path of movement at a selected speed, said motor being actuated to operate at said selected speed in response to an application of multiphase pulse width modulated signals thereto, said motor developing a torque in response to movement of said tool;

a driver connected to said motor, said driver including a plurality of transistors that are selectively switched between a voltage source and ground to generate a plurality of pulse width modulated signals for application to said motor, said transistors being switched in response to the application of driver control signals thereto and said transistors having a current flowing therethrough representative of said torque developed by said motor;

a speed sensor connected to said motor for monitoring said speed of said motor and producing a speed signal representative of said speed of said motor;

a current sensor connected to said driver transistors for producing a transistor current signal representative of said current flowing through said transistors;

a speed regulator connected to said speed sensor for receiving said speed signal, said speed regulator being configured to compare said speed signal to a speed setpoint speed signal representative of a selected motor speed and to produce a speed error signal based on said comparison;

a torque regulator connected to said speed regulator for receiving said speed error signal, said torque regulator being configured to compare said speed error signal to a torque limit signal representative of a selected maximum torque and to produce a selectively adjusted speed error signal based on said comparison; and a driver controller connected to said current sensor for receiving said transistor current signal and to said torque controller for receiving said adjusted speed error signal and to said driver, said driver controller being configured to compare said transistor current signal with said adjusted speed error and to produce said driver control signals in response to said comparison, wherein said driver control signals are of a sufficient potential so that said transistors alternatively connect said motor between the voltage source and ground.

15. The medical instrument of claim 14, wherein said torque controller is configured to selectively attenuate said speed error signal to produce said adjusted speed error signal when said speed error signal exceeds said torque limit signal.

16. The medical instrument of claim 14, wherein said tool has a longitudinal axis and said motor is coupled to said tool so as to rotate said tool along said longitudinal axis.

17. The medical instrument of claim 14, wherein said tool is a drill.

18. A medical instrument including:

a tool;

a motor coupled to said tool for driving said tool through a repetitive path of movement at a selected speed, said motor being actuated to operate at said selected speed in response to an application of a variable motor energization signal thereto;

a speed monitor connected to said motor for producing a motor speed signal representative of said speed of said motor;

a motor controller connected to said motor for applying said motor energization signal thereto and to said speed monitor for receiving said motor speed signal therefrom, said motor controller being configured to compare said speed signal to a speed setpoint signal and, in response to said comparison, to vary said motor energization signal to cause said motor to operate at a selected speed; and an instrument control assembly including:

a maximum speed input device for generating a maximum speed signal in response to the inputting of a user-selected maximum tool speed;

a speed control input device for generating a user speed signal in response to the inputting of a user-selected real time speed command; and an instrument controller connected to said speed monitor to receive said motor speed signal, to said maximum speed input device for receiving said maximum speed signal, to said speed control input device for receiving said user speed signal and to said motor controller, said instrument controller being configured to generate said speed setpoint signal for application to said motor controller as a function of said user speed signal and a variable function ratio and to compare said user speed signal to said maximum speed signal wherein, when said comparison of said user speed signal to said maximum speed signal indicates said motor is to be operated at the maximum speed, said instrument controller is further configured to compare said motor speed signal to said maximum speed signal and, based on said comparison, to adjust said function ratio.

19. The medical instrument of claim 18, wherein:

said motor develops a torque as a result of the movement of said tool;

said instrument further includes a torque monitor connected to said motor for monitoring said motor torque, said torque monitor being configured to generate a motor torque signal representative of said motor torque;

said instrument control assembly further includes a torque input device for generating a maximum torque signal in response to a user-selected maximum torque command; and said instrument controller is connected to said torque monitor for receiving said torque signal and to said torque input device for receiving said maximum torque signal and is further configured to compare said motor torque signal to said maximum torque signal, wherein when said comparison indicates said motor torque is greater than said user-selected maximum torque, said instrument controller bypasses said adjustment of said function ratio.

20. The medical instrument of claim 19, wherein said motor controller is connected to said torque monitor for receiving said motor torque signal and to said torque input device for receiving said maximum torque signal and said motor control is further configured to compare said motor torque signal to said maximum torque signal and to vary said motor energization signal based on said comparison.

21. The medical instrument of claim 20, wherein said motor controller is connected to said motor to function as said speed monitor and said instrument controller is connected to said motor controller for receiving said motor speed signal and said motor torque signal therefrom.

22. The medical instrument of claim 19, further including:

a gear reduction unit for coupling said tool to said motor, said gear reduction unit being configured to establish one of a plurality of gear reduction ratios between said motor and said tool so that said tool is actuated at a speed relative to said speed of said motor that is representative of a selected said gear reduction ratio; and said instrument controller is connected to said gear reduction unit for establishing said selected reduction ratio in response to a user selection and said instrument controller is further configured to at least modulate said maximum torque signal as a function of the user-selected gear reduction ratio.

23. The medical instrument of claim 22, wherein said motor controller is connected to said torque monitor for receiving said motor torque signal and to said instrument controller for receiving said modulated maximum torque signal and said motor control is further configured to compare said motor torque signal to said maximum torque signal and to vary said motor energization signal based on said comparison.

24. The medical instrument of claim 19, wherein said tool has a longitudinal axis and said motor is coupled to said tool so as to rotate said tool along said longitudinal axis.

25. The medical instrument of claim 19, wherein said motor is a brushless motor.

26. The medical instrument of claim 18, wherein said motor is a brushless motor.

27. The medical instrument of claim 18, wherein said tool has a longitudinal axis and said motor is coupled to said tool so as to rotate said tool along said longitudinal axis.

28. The medical instrument of claim 18, wherein said motor controller is connected to said motor to function as said speed monitor and said instrument controller is connected to said motor controller for receiving said motor speed signal therefrom.

29. A method of regulating the speed of motor of a medical instrument, the medical instrument having a tool attached to the motor, the motor being designed to operate at selected speeds in response the application of a modulated power signal thereto, said method including the steps of:

generating a motor speed signal representative of the speed of the motor;

generating a maximum speed signal representative of a maximum speed at which the motor is to operate;

generating a user speed signal representative of a speed which the user wants the motor to operate at;

comparing said user speed signal to said maximum speed signal;

when said user speed signal-maximum speed signal comparison indicates said motor is to operate below said maximum speed, generating a speed setpoint signal as a function of a said user speed signal and a function ratio;

applying said motor speed signal and said speed setpoint signal to a motor controller, said motor controller comparing said motor speed signal and said speed setpoint signal and, based on said comparison, generating a modulated power signal for application to the motor;

when said user speed-maximum speed comparison indicates the motor is to be operated at the user-selected maximum speed, generating a speed setpoint signal based on said function ratio that is representative of said maximum speed, applying said maximum speed setpoint signal to said motor controller and comparing said motor speed signal to said maximum speed and based on said motor speed signal-maximum speed signal comparison, adjusting said function ratio to cause the generation of a speed setpoint signal that causes said motor to operate at said maximum speed.

30. The method of medical instrument motor speed regulation of claim 29, further including the steps of:

generating a maximum torque signal representative of a maximum torque at which the motor is to operate;

generating a motor torque signal representative of the torque produced by said motor;

comparing said motor torque signal to said maximum torque signal; and when said motor torque signal/maximum torque signal comparison indicates the motor torque exceeds the selected maximum torque, bypassing said adjustment of said transfer function ratio.

* * * * *